(12) United States Patent
Wietelmann et al.

(10) Patent No.: US 6,713,642 B2
(45) Date of Patent: Mar. 30, 2004

(54) METHOD FOR PRODUCING ALKALI METAL MONOHYDRIDOBORATES AND MONOHYDRIDOALUMINATES

(75) Inventors: Ulrich Wietelmann, Friedrichsdorf (DE); Dieter Hauk, Friedberg (DE); Andre Majdalani, Kronberg (DE); Uwe Lischka, Niedereschbach (DE)

(73) Assignee: Chemetall GmbH, Frankfurt am Main (DE)

( * ) Notice: Subject to any disclaimer, the term of this patent is extended or adjusted under 35 U.S.C. 154(b) by 0 days.

(21) Appl. No.: 10/240,706

(22) PCT Filed: Mar. 20, 2001

(86) PCT No.: PCT/EP01/03161

§ 371 (c)(1),
(2), (4) Date: Feb. 25, 2003

(87) PCT Pub. No.: WO01/77117

PCT Pub. Date: Oct. 18, 2001

(65) Prior Publication Data

US 2003/0166956 A1 Sep. 4, 2003

(30) Foreign Application Priority Data

Apr. 5, 2000 (DE) .......................... 100 16 802

(51) Int. Cl.⁷ .............. C07F 5/06; C07F 5/02
(52) U.S. Cl. .......... 556/182; 556/170; 556/187; 568/1; 568/8
(58) Field of Search ............... 556/170, 182, 556/187; 568/1, 8

(56) References Cited

PUBLICATIONS

"Additional compounds of alkali metal hydrides", Brown, vol. 100. No. 11, 1978.
"Houben–Weil—Methoden . . . Triorganoboranen", Koster, 1983.

*Primary Examiner*—Porfirio Nazario-Gonzalez
(74) *Attorney, Agent, or Firm*—Fulbright & Jaworski L.L.P.

(57) ABSTRACT

The invention relates to a method for producing compounds of general formula (A) by reacting an alkali metal hydride with a compound (B) during which the reaction is carried out in the presence of a catalyst that contains boron, whereby: M represents Li, Na, K, Rb or Cs; E represents B or Al, and; $X^1$, $X^2$, $X^3$, independent of one another, represent a secondary or tertiary alkyl group, which is comprised of 2 to 10 atoms, or represent a phenyl group which itself can be alkyl-substituted or they represent an alkoxy group, and the catalyst, which contains boron, or the conversion product thereof with MH is capable of acting as a hydride transfer agent.

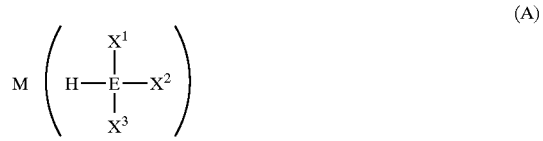

(A)

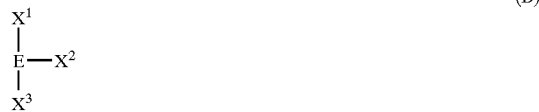

(B)

12 Claims, No Drawings

METHOD FOR PRODUCING ALKALI METAL MONOHYDRIDOBORATES AND MONOHYDRIDOALUMINATES

The invention relates to a process for the preparation of alkali metal monohydridoboranates and -aluminates of the general formula:

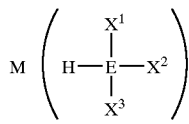
(A)

wherein

M=Li, Na, K, Rb or Cs and

E=B or Al, and $X^1$, $X^2$, $X^3$=in each case independently of one another, is a 2 to 10 C atom secondary or tertiary alkyl group or a phenyl group, which in its turn can be alkyl-substituted, or an alkoxy group.

Alkali metal monohydridoboranates and -aluminates are to some extent known classes of compounds, the members of which have found uses as reagents in chemical synthesis, e.g. as reducing agents. Thus, for example, commercially available lithium tri-tert-butoxyaluminium hydride is employed for the chemoselective reduction of acid chlorides to aldehydes or for the stereoselective reduction of asymmetrically substituted or cyclic ketones to alcohols (P. Galatsis, "Lithium-tri-tert-butoxyaluminiumhydride in L. A. Paquette, Encyclopaedia of Reagents for Organic Synthesis, J. Wiley & Sons, Chichester 1995, p. 3168–3172).

In a similar manner, trialkyl borohydrides also serve as diversely usable reducing agents in organic synthesis. In general, their stereoselectivity increases with the steric bulkiness of the alkyl substituents. (H. C. Brown, S. Krishnamurthy, J. L. Hubbard, J. Am. Chem. Soc. 1978, 100, 3343; R. Köster, "Anionische Organobor-Wasserstoff-Verbindungen [Anionic Organoboron-Hydrogen Compounds]" in: Houben-Weyl, Methoden der organischen Chemie [Methods of Organic Chemistry] 13/3b, p. 798–813, G. Thieme Verlag, Stuttgart, 1983; J. L. Hubbard, "Lithium tri-s-butylborohydride" in: L. A. Paquette, Encyclopaedia of Reagents for Organic Synthesis, J. Wiley & Sons, Chichester 1995, 3172–3176; J. D. Odom, in: Comprehensive Organometallic Chemistry, G. Wilkinson (ed.), Pergamon Press 1982, vol. 1, p. 297).

Some representatives of the alkali metal monohydridoboranates and -aluminates can be obtained by addition of alkali metal hydride (MH) to the $EX^1X^2X^3$ compound. This applies e.g. to the preparation of Li[HBEt$_3$] in accordance with:

(1)

where Et=ethyl.

Without a solvent or with a hydrocarbon as the solvent, the reaction at 200° C. takes approx. 4 h, and with Et$_2$O as the solvent the reaction on heating under reflux takes approx. 24 h (R. Köster, "Anionische Organobor-Wasserstoff-Verbindungen" in: Houben-Weyl, Methoden der organischen Chemie 13/3b, p. 798–813, G. Thieme Verlag, Stuttgart, 1983). In THF solution, the addition can be effected within one day at room temperature.

The induction time of the reaction presents problems. This method also fails if boranes with bulky substituents are employed. For example, the reaction of B($^s$Bu)$_3$ with alkali metal hydrides in boiling THF gives a conversion of only 10% after 24 h, and for this reason this reaction is unsuitable for a commercial synthesis. (H. C. Brown, S. Krishnamurthy, J. L. Hubbard, J. Am. Chem. Soc. 1978, 100, 3343; R. Köster, "Anionische Organobor-Wasserstoff-Verbindungen" in: Houben-Weyl, Methoden der organischen Chemie 13/3b, p. 798–813, G. Thieme Verlag, Stuttgart, 1983; J. L. Hubbard, "Lithium tri-s-butylborohydride" in: L. A. Paquette, Encyclopaedia of Reagents for Organic Synthesis, J. Wiley & Sons, Chichester 1995, 3172–3176; J. D. Odom, in: Comprehensive Organometallic Chemistry, G. Wilkinson (ed.), Pergamon Press 1982, vol. 1, p. 297).

Boranes with even bulkier substituents are inert with respect to "normal", i.e. commercially obtainable, NaH and LiH in boiling THF. This does not apply to the highly reactive form of the binary hydrides, such as are prepared e.g. by decomposition of alkyllithium solutions under a hydrogen atmosphere. (R. Pi, T. Friedl and P. v. R. Schleyer, J. Org. Chem. 1987, 52, 4299–4304). Because the active metal hydride first has to be prepared from expensive organolithium solutions, this process is of little commercial interest.

Another variant of preparing active metal hydride comprises preparing the metal, preferably in finely divided form, in the presence of a trisubstituted boron compound, so that the hydride MH formed in situ can add on to the boron compound, immediately, to form a borohydride of the formula M[R$^1$R$^2$R$^3$B]H. Disadvantages in this case are that the metal must be present in the form of a highly reactive powder which is difficult to handle, and a catalyst combination in the form of a transition metal salt (e.g. FeCl$_3$) and/or polyaromatics (e.g. phenanthrene) must be employed to achieve reasonable reaction temperatures and times (U.S. Pat. No. 5,886,229). The product solutions accordingly are contaminated and are discoloured by the transition metal content.

Trialkoxy-element hydrides with bulky substituents also do not react or react only extremely slowly with MH. For example, the preparation of lithium tri-tert-butoxyaluminium hydride (LTTBA) in accordance with:

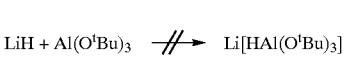
(2)

is unknown (see also Comparative Example A).

Since the direct preparation is not possible, a number of process alternatives have been developed. Thus, LTTBA is prepared by alcoholysis of lithium aluminium hydride in accordance with:

(3)

The high preparation costs are a disadvantage, since relatively expensive hydride hydrogen in the LiAlH$_4$ is destroyed by the alcoholysis.

Trialkyl borohydrides with bulky organic radicals are prepared by one of the following general processes:

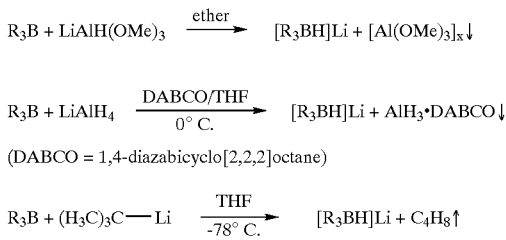

$$R_3B + LiAlH(OMe)_3 \xrightarrow{\text{ether}} [R_3BH]Li + [Al(OMe)_3]_x \downarrow \quad (4)$$

$$R_3B + LiAlH_4 \xrightarrow[0°C.]{\text{DABCO/THF}} [R_3BH]Li + AlH_3 \cdot DABCO \downarrow \quad (5)$$

(DABCO = 1,4-diazabicyclo[2,2,2]octane)

$$R_3B + (H_3C)_3C-Li \xrightarrow[-78°C.]{\text{THF}} [R_3BH]Li + C_4H_8 \uparrow \quad (6)$$

Disadvantageous with the process according to (4) are the use of expensive LiAlH(OMe)$_3$, which is not commercially obtainable, and above all the fact that large amounts of insoluble aluminium methylate are obtained, which makes preparation of the trialkyl borohydride in a pure form extremely difficult. Similar circumstances apply to process (5), and in addition there are high costs for the donor, such as e.g. 1,4-diazabicyclo[2,2,2]octane (DABCO).

Process (6) has the disadvantage that expensive t-butyllithium is used as the LiH source, a gaseous by-product being formed. Furthermore, the reaction must be carried out at very low temperatures, which is very unfavourable in energy terms.

All the processes (3)–(6) have the disadvantage that they are limited in practice to the preparation of the lithium derivative, since only the corresponding lithium raw materials (and not the Na or K compounds) are commercially obtainable. The addition of higher alkali metal hydrides (NaH, KH, RbH, CsH) to a starting compound EX$^1$X$^2$X$^3$ indeed proceeds substantially faster than in the case of LiH, but in these cases also the rate of reaction decreases sharply with increasing volume of the substituents X (see comparison example B).

The object of the invention is to overcome the disadvantages of the prior art and to provide a process for the rapid preparation of alkali metal monohydridoboranates and -aluminates of the general formula:

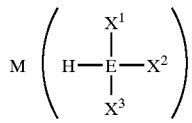 (A)

at mild temperatures which starts from commercially available alkali metal hydride, allows a reaction procedure without increased pressure and avoids the formation of insoluble by-products.

The object is achieved by the process described in claim 1. Claims 2 to 11 develop the process described. Claim 12 describes preferred process products.

It has been found that the addition described above of alkali metal hydride (MH) on to an EX$^1$X$^2$X$^3$ compound is significantly accelerated by a catalyst:

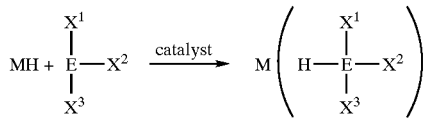

where
M=Li, Na, K, Rb or Cs and
E=B or Al and

X$^1$, X$^2$, X$^3$, in each case independently of one another, = a secondary or tertiary alkyl group consisting of 2 to 10 C atoms or
a phenyl group, which in its turn can be alkyl-substituted, or
an alkoxy group.

Any boron-containing compound which contains the structural unit BH$_3$ and which itself or the reaction product of which with MH is capable of acting as a hydride transfer agent can be employed as the catalyst.

X$^1$, X$^2$ and X$^3$, in each case independently of one another, can preferably be iso-propyl or sec-butyl or tert-butyl or tert-amyl or siamyl (sec-2-methyl-butyl) or a phenyl group, which in its turn can be alkyl-substituted, or the following alkoxy group:

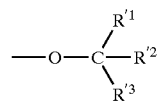

where R$'^1$, R$'^2$, R$'^3$, independently of one another, =alkyl having 1 to 10 C atoms.

In the case of liquid compounds EX$^1$X$^2$X$^3$, the reaction can in principle be carried out without a solvent; however, working in a solvent is preferred, or unavoidable in cases where EX$^1$X$^2$X$^3$ is not liquid. Aprotic organic compounds, such as e.g. hydrocarbons and/or ethers, are used as the solvent. The reaction proceeds faster in polar solvents than in non-polar hydrocarbons.

In principle, the sequence of the addition of the individual reaction partners plays no role. Preferably, the total amount of MH is suspended in the solvent, the catalyst is added and the compound EX$^1$X$^2$X$^3$ is metered in as a function of the rate of reaction.

Borane complexes H$_3$B.D with a donor compound D are particularly suitable as the catalyst. Amines, preferably secondary amines, can be employed e.g. as the donor compound.

Aminoborohydrides of the general formula:

 (D)

$$M[R^2R^1NBH_3]_n \quad (D)$$

where M=Li, Na, K, Rb, Cs or Mg halogen if n=1, or M=Mg if n=2 and
R$^1$, R$^2$=independently of one another H, alkyl or aryl,
wherein R$^1$ and R$^2$ can be bonded to one another via a ring closure, or $$M[R^2R^1NBH_2NR^3R^4BH_3]_n \quad (E)$$

where M=Li, Na, K, Rb, Cs or Mg halogen if n=1 or M=Mg if n=2 and
R$^1$, R$^2$, R$^3$, R$^4$=independently of one another H, alkyl or aryl, wherein R$^1$, R$^2$, R$^3$ and/or R$^4$ can be bonded to one another via a ring closure,
can also be employed as the catalyst.

The catalyst is in general employed in an amount of 0.1 to 20 mol %, and in individual cases it may prove favourable to choose an even higher dosage. The catalyst is preferably employed in an amount of 0.5 to 5 mol %.

The temperature of the reaction is 0 to 150° C., depending on the substrate and solvent.

The process according to the invention has the advantage that alkali metal monohydridoboranates and -aluminates can be prepared from commercial alkali metal hydrides in a simple manner, rapidly and without the use of pressure. In particular, the alkali metal monohydridoboranates and -aluminates with sterically voluminous substituents are accessible to synthesis in this manner.

An alkali metal tri-tert-butoxyaluminium hydride or an alkali metal tri-sec-butyl borohydride or alkali metal tri-(sec-2-methyl-butyl)-borohydride can preferably be obtained as compound (A) by the process according to the invention.

The alkali metal monohydridoboranates and -aluminates prepared by the process according to the invention are used as reducing agents in organic synthesis.

The invention is explained in more detail in the following with the aid of examples.

EXAMPLE 1

Preparation of Lithium Tri-tert-butoxyaluminium Hydride Li[HAl(O$^t$Bu)$_3$] in THF/toluene with the Catalyst Lithium Dimethylaminoborohydride Li[Me$_2$NBH$_3$] (LiDMAB)

The catalyst solution was first prepared as follows: 7.41 g (1.07 mol) lithium metal granules were suspended in 277 g anhydrous THF in a 1 l reactor. A mixture comprising 68 g dimethylaminoborane (DMAB), 39.5 g isoprene and 116 g THF was then metered in, while stirring, in the course of 2 hours. The reactor internal temperature was adjusted to 22 to 27° C. by external cooling.

After an after-reaction time of two hours at approx. 25° C., the small residues of lithium metal were filtered off.

Yield:

363 g with a Li content of 1.89% (corresponds to

92% of theoretical)

$\delta^{11}$B: 14.2 ppm, quartet 243 g of a 24.9% Al(O$^t$Bu)$_3$ solution (242 mmol) in THF/toluene were initially introduced into a 1 l double-walled reactor with an intensive cooler, KPG stirrer and thermocouple, 2.2 g (278 mmol) LiH powder and 2.0 g of the solution of LiDMAB in THF prepared above (concentration 2.7 mmol/g, 2.0 g solution correspond to 5.6 mmol LiDMAB=2.3 mol %, based on the educt) were added and the mixture was heated under reflux.

After two and three hours, respectively, samples were taken and tested for the progress of the reaction by $^{27}$Al-NMR. It was found here that the reaction was already substantially concluded after one hour. After 2 hours the desired product ($\delta^{27}$Al=78.2 ppm) was formed with a spectroscopic purity of ≧90%. The cloudy solution was filtered over a G2 glass filter frit (30 min) and analysed.

Yield:

284 g of clear yellowish solution

Gas volumetry:

H=0.781 mmol/g^222 mmol (^92% of theoretical)

Comparative Example A

Preparative Experiment for Li[HAl(O$^t$Bu)$_3$], without Catalyst 35 g of a 30% solution of aluminium tert-butylate (corresponds to 43 mmol) in THF/toluene (1:1.6) were initially introduced into a 100 ml 2-necked Schlenk flask with a reflux condenser and temperature probe, and 0.70 g (88 mmol) of ground lithium hydride was added. The mixture was refluxed for three hours (internal temperature 97° C.).

After cooling to room temperature, a sample was investigated:

Gas volumetry (filtered sample): not detectable $\delta^{27}$Al: 49.1 ppm (of Al(O$^t$Bu)$_3$)

no traces of the product peak at 78 ppm

EXAMPLE 2

Preparation of Lithium Tri-sec-butyl Borohydride in THF with the Catalyst LiDMAB 7.5 g LiH (0.94 mol) were suspended in 540 g THF in a 1 l double-walled reactor and 8.0 g of the catalyst solution prepared in Example 1 (concentration 1.05 mmol/g, 8.0 g solution correspond to 8.4 mmol LiDMAB=0.96 mol %, based on the educt) were added. Thereafter, metering in of tri-sec-butylborane (159 g, 875 mmol in total) was started. During this, the reaction temperature rose from approx. 25 to >30° C. When the addition had ended, the mixture was boiled under reflux for 1 hour.

After cooling, the solution was filtered over a glass frit.

Yield:

690 g of solution with 1.23 mmol/g active hydrogen content (97% of theoretical)

$\delta^{11}$B: −6.8 ppm, d$^1$J(B—H)=540 Hz

Purity (based on the boron species): approx. 97%

EXAMPLES 3 TO 7

Preparation of Lithium Tri-sec-butyl Borohydride in Various Solvents and with Various Catalysts.

Analogously to Example 2, lithium tri-sec-butyl borohydride was prepared in various solvents and with various catalysts. Further details are to be found in Table 1.

The catalyst MgDMAB (ClMg[Me$_2$NBH$_3$]) was prepared as follows:

2.95 g (50 mmol) dimethylaminoborane were dissolved in 8.5 g THF in a 0.1 l flask and the solution was cooled to approx. 10° C. with a water bath. 19.2 g of a 25% ethylmagnesium chloride solution (54 mmol) were metered in with a syringe in the course of 15 minutes. During this, the reaction mixture heated up to 35° C. A gas (ethane) escaped.

After the mixture had been stirred for one hour at room temperature, a sample was taken and investigated by NMR spectroscopy.

$\delta^{11}$B: 15.5 ppm (quartet)

EXAMPLES 8 AND 9 AND COMPARATIVE EXAMPLE B

Preparation of Sodium Tri-sec-butyl Borohydride in Various Solvents and with Various Catalysts and without a Catalyst Analogously to Example 2 sodium tri-sec-butyl borohydride was prepared in various solvents and with various catalysts. Further details are to be found in Table 2.

The catalyst NaDADB (sodium diaminodiborate, Na[Me$_2$NBH$_2$NMe$_2$BH$_3$]) was prepared as follows:

46.4 g of a mixture of sodium and aluminium oxide (9.2% Na, corresp. to 171 mmol) were suspended in 150 ml THF in a 250 ml two-necked flask, and a solution of 10.4 g (176 mmol) dimethylaminoborane (DMAB) in 60 ml THF was added, while stirring, in the course of 100 min. The reaction mixture heated up to 38° C., with sometimes vigorous evolution of gas (hydrogen). After the mixture had been after-stirred for one hour at room temperature, the Al$_2$O$_3$ was filtered off.

146 g of a solution with an Na content of 0.52 mmol/g were obtained.

(Yield: 86%, based on DMAB)

$\delta^{11}$B: 2.1 ppm (triplet); 14.3 ppm (quartet) intensity ratio 1:1

TABLE 1

Preparation of lithium tri-sec-butyl borohydride

| | Starting substances | | | Catalyst | | | Reaction | | |
|---|---|---|---|---|---|---|---|---|---|
| | $B(^sBu)_3$ | LiH | | | Amount | | time | temp. | Yield[2] |
| Eg. | g/mmol | mmol | Nature[1] | mmol/ | mol % | Solvent | min | ° C. | % |
| 3 | 9.2/50 | 64 | LiDMAB | 4.9 | 10 | 1,2-dimethoxy- | 15 | 60 | 28 |
| 4 | 27.6/152 | 180 | LiDMAB | 9 | 6 | ethane $Et_2O$/THF (5.5:1) | 180 | approx. 45 | 42 |
| 5 | 4.6/25 | 27 | LiMAB | 4 | 16 | THF | 15 700 | 65 25 | 51 98 |
| 6 | 9.1/50 | 64 | MgDMAB | 5.1 | 5 | THF | 120 | 65 | 100 |
| 7 | 9.8/54 | 60 | DMAB | 5.3 | 5 | THF | 120 | 65 | 100 |

[1])LiDMAB = Li [$Me_2NBH_3$]
LiMAB = Lithium morpholinoborohydride, preparation analogously to LiDMAB according to Example 1
MgDMAB = ClMg [$Me_2NBH_3$]
DMAB = $Me_2NHBH_3$
[2])According to $^{11}$B-NMR spectroscopy

TABLE 2

Preparation of sodium tri-sec-butyl borohydride

| | Starting substances | | Catalyst | | | Reaction | | |
|---|---|---|---|---|---|---|---|---|
| | $B(^sBU)_3$ | NaH | | Amount | | time | temp. | Yield[2] |
| Example | g/mmol | mmol | Nature[1] | mmol/l | mol % | min | ° C. | % |
| 8 | 16.9/93 | 100 | LiDMAB | 7.8 | 8 | 10 | 20–65[3] | 100 |
| 9 | 14.6/80 | 100 | NaDADB | 5.6 | 7 | 10 | 20–65[3] | 100 |
| B | 14.6/80 | 100 | ./. | ./. | ./. | 40 100 | 65 65 | 90 97 |

[1])LiDMAB = Li [$Me_2NBH_3$]
NaDADB = Na ($Me_2NBH_2NMe_2BH_3$)
[2])According to $^{11}$B-NMR spectroscopy
[3])After addition of the catalyst the reaction mixture heats up briefly to the boiling point without an external supply of heat It can be seen from Examples 3 and 4 (Table 1) that in addition to pure THF or a THF/toluene mixture (as in the preceding examples 1 and 2), 1,2-dimethoxyethane and THF/diethyl ether mixtures can also be used as the solvent.

Example 5 shows the possible use of a lithium aminoborohydride catalyst with a cyclic amino radical. In this case the reaction was also carried out at two different temperatures: initially at the boiling point, only 15 minutes being required for an approx. 50% degree of conversion. The remainder of the reaction was effected by stirring at room temperature (over a correspondingly longer period of time).

Examples 6 and 7 show the use of various other catalysts. Both chloromagnesium aminoborohydride and dimethylaminoborane lead to a quantitative conversion to the desired product in boiling THF in the course of 2 hours.

Experiments for the preparation of sodium tri-sec-butyl borohydride are described in Examples 8 and 9 and Comparative Example B (Table 2). Without a catalyst (Comparative Example B), the mixture must be refluxed for about 40 minutes in order to achieve a 90% degree of conversion. However, the reaction is considerably faster than in the analogous preparation of the lithium derivative (10% conversion after stirring under reflux conditions for 24 hours).

If catalysts such as LiDMAB or a diaminodiboranate (Examples 8 and 9) are employed according to the invention to accelerate the reaction, a considerable shortening of the reaction times is to be observed. The activity of the catalysts also manifests itself in that the reaction mixtures heat up to the boiling point directly after the addition, without external action of heat; this indicates an extremely fast reaction.

What is claimed is:

1. A process for the preparation of compounds of the formula:

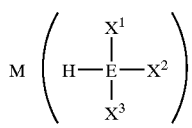

(A)

comprising reacting an alkali metal hydride with a compound of formula (B):

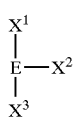

(B)

in the presence of a boron-containing catalyst; wherein
M is Li, Na, K, Rb or Cs; and
E is B or Al; and
$X^1$, $X^2$, $X^3$=are each independently
a 2 C to 10 C secondary or tertiary alkyl group or
a phenyl group, which can be alkyl-substituted, or an alkoxy group; and wherein
the boron-containing catalyst contains the structural unit BH$_3$ and the boron-containing catalyst or reaction product thereof with MH being capable of acting as a hydride transfer agent.

2. A process according to claim 1, wherein $X^1$, $X^2$, $X^3$ are independently iso-propyl or sec-butyl or tert-butyl or tert-amyl or siamyl (sec-2-methyl-butyl) or a phenyl group, which in its turn can be alkyl-substituted, or

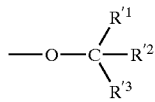

wherein $R^1$, $R^2$, $R^3$ are independently an alkyl having 1 C to 10 C atoms.

3. A process according to claim 1, wherein
the reaction is carried out in an aprotic organic solvent.

4. A process according to claim 3, wherein said solvent is polar.

5. The process according to claim 1, wherein
the boron-containing catalyst is a borane complex of formula:

$$H_3B.D \quad (C)$$

wherein D is a donor compound.

6. The process according to claim 5, wherein the donor compound is an amine.

7. The process according to claim 6, wherein
the donor compound is a secondary amine.

8. The process according to claim 1, wherein the catalyst is an aminoborohydride of the formula:

$$M[R^2R^1NBH_3]_n \quad (D)$$

wherein

M is Li, Na, K, Rb, Cs or Mg halogen if n is 1 or M is Mg if n is 2; and $R^1$ and $R^2$ are independently H, C1 to C10 alkyl or aryl, wherein $R^1$ and $R^2$ can be bonded to one another to form a closed ring.

9. The process according to claim 1, wherein the catalyst is an aminoborohydride of the formula:

$$M[R^2R^1NBH_2NR^3R^4BH_3]_n \quad (E)$$

wherein

M is Li, Na, K, Rb, Cs or Mg halogen if n is 1 or M is Mg if n is 2; and $R^1$, $R^2$, $R^3$, $R^4$ are independently H, C1 to C10 alkyl or aryl, wherein $R^1$, $R^2$, $R^3R^4$ can be bonded to one another to form a closed ring.

10. The process according to claim 1, wherein
the catalyst is present in an amount of 0.1 to 20 mol %.

11. The process according to claim 10, wherein the catalyst is present in an amount of 0.5 to 5 mol %.

12. The process according to claim 1, wherein
compound A is an alkali metal tri-tert-butoxyaluminium hydride or an alkali metal tri-sec-butyl borohydride or alkali metal tri-(sec-2-methyl-butyl) borohydride.

* * * * *